United States Patent
Sianawati et al.

(10) Patent No.: US 8,592,405 B2
(45) Date of Patent: Nov. 26, 2013

(54) SYNERGISTIC ANTIMICROBIAL COMPOSITION

(75) Inventors: Emerentiana Sianawati, Vernon Hills, IL (US); Sangeeta S. Ganguly, Chicago, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/389,088

(22) PCT Filed: Jul. 28, 2010

(86) PCT No.: PCT/US2010/043518
§ 371 (c)(1),
(2), (4) Date: Feb. 6, 2012

(87) PCT Pub. No.: WO2011/017156
PCT Pub. Date: Feb. 10, 2011

(65) Prior Publication Data
US 2012/0135974 A1    May 31, 2012

Related U.S. Application Data

(60) Provisional application No. 61/273,530, filed on Aug. 5, 2009, provisional application No. 61/331,423, filed on May 5, 2010.

(51) Int. Cl.
*A01N 47/10* (2006.01)
*A01N 43/78* (2006.01)
*A01N 47/30* (2006.01)
*A01N 43/80* (2006.01)
*A01N 55/02* (2006.01)
*A01P 1/00* (2006.01)

(52) U.S. Cl.
USPC ........... 514/188; 514/479; 514/372; 514/365; 514/596

(58) Field of Classification Search
None
See application file for complete search history.

(56) References Cited

U.S. PATENT DOCUMENTS

| 5,591,760 A | 1/1997 | Hsu |
| 6,197,805 B1 | 3/2001 | Smith |
| 6,846,777 B2 | 1/2005 | Antoni-Zimmermann et al. |
| 2003/0234068 A1* | 12/2003 | Swofford et al. ............... 156/39 |
| 2004/0138217 A1* | 7/2004 | Bruns et al. ................ 514/235.8 |
| 2008/0108680 A1* | 5/2008 | Bruns et al. .................. 514/383 |
| 2008/0160288 A1* | 7/2008 | Kingma et al. ............... 428/326 |

FOREIGN PATENT DOCUMENTS

EP    180313    5/1986

* cited by examiner

*Primary Examiner* — Ernst Arnold
*Assistant Examiner* — Jianfeng Song
(74) *Attorney, Agent, or Firm* — Kenneth Crimaldi

(57) ABSTRACT

A synergistic antimicrobial composition containing 3-iodo-2-propynyl-butylcarbamate and fluometuron.

3 Claims, No Drawings

SYNERGISTIC ANTIMICROBIAL COMPOSITION

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, e.g., those resistant to some antimicrobial compounds. Combinations of different antimicrobial compounds are sometimes used to provide overall control of microorganisms in a particular end use environment. For example, U.S. Pat. No. 6,197,805 discloses a combination of 3-iodo-2-propynyl-butylcarbamate (IPBC) and 2-(methoxycarbonylamino)benzimidazole, but this reference does not suggest any of the combinations claimed herein. Moreover, there is a need for additional combinations of antimicrobial compounds having enhanced activity against various strains of microorganisms to provide effective control of the microorganisms, especially in dry film coatings. The problem addressed by this invention is to provide such additional combinations of antimicrobial compounds.

STATEMENT OF THE INVENTION

The present invention is directed to a synergistic antimicrobial composition comprising: (a) 3-iodo-2-propynyl-butylcarbamate; and (b) fluometuron; wherein a weight ratio of 3-iodo-2-propynyl-butylcarbamate to fluometuron is from 10:1 to 1:10.

The present invention is further directed to a synergistic antimicrobial composition comprising: (a) 3-iodo-2-propynyl-butylcarbamate; (b) fluometuron; and (c) 4,5-dichloro-2-n-octyl-4-isothiazolin-3-one (DCOIT); wherein a weight ratio of 3-iodo-2-propynyl-butylcarbamate to fluometuron is from 3:1 to 1:2; and a weight ratio of 3-iodo-2-propynyl-butylcarbamate to 4,5-dichloro-2-n-octyl-4-isothiazolin-3-one is from 8:1 to 4:1.

The present invention is further directed to a synergistic antimicrobial composition comprising: (a) 3-iodo-2-propynyl-butylcarbamate; (b) fluometuron; and (c) diiodomethyl-p-tolylsulfone (DIMTS); wherein a weight ratio of 3-iodo-2-propynyl-butylcarbamate to fluometuron is from 3:1 to 1:2; and a weight ratio of 3-iodo-2-propynyl-butylcarbamate to diiodomethyl-p-tolylsulfone is from 8:1 to 4:1.

The present invention is further directed to a synergistic antimicrobial composition comprising: (a) fluometuron; and (b) 2-n-octyl-4-isothiazolin-3-one (OIT); wherein a weight ratio of fluometuron to OIT is from 1:1 to 1:2.

The present invention is further directed to a synergistic antimicrobial composition comprising: (a) fluometuron; and (b) zinc pyrithione (ZPT); wherein a weight ratio of fluometuron to ZPT is from 10:1 to 1:15.

The present invention is further directed to a synergistic antimicrobial composition comprising: (a) fluometuron; and (b) thiabendazole (TBZ); wherein a weight ratio of fluometuron to TBZ is from 10:1 to 1:15.

The present invention is further directed to a synergistic antimicrobial composition comprising: (a) fluometuron; and (b) diiodomethyl-p-tolylsulfone (DMITS); wherein a weight ratio of fluometuron to DMITS is from 10:1 to 1:15.

DETAILED DESCRIPTION OF THE INVENTION

As used herein, the following terms have the designated definitions, unless the context clearly indicates otherwise. Fluometuron is 1,1-dimethyl-3-($\alpha,\alpha,\alpha$-trifluoro-m-tolyl)urea. The term "antimicrobial compound" refers to a compound capable of inhibiting the growth of or controlling the growth of microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, ATCC=American Type Culture Collection, and MIC=minimum inhibitory concentration. Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present.

In some embodiments of the invention in which the antimicrobial composition comprises IPBC and fluometuron, a weight ratio of IPBC to fluometuron is from 8:1 to 1:7, preferably from 6:1 to 1:5, preferably from 5:1 to 1:5; preferably from 6:1 to 1:4, preferably from 5:1 to 1:4; preferably from 4:1 to 1:4; preferably from 5:1 to 1:3; preferably from 4:1 to 1:3.

In some embodiments of the invention in which the antimicrobial composition comprises IPBC, fluometuron and DCOIT, a weight ratio of IPBC to fluometuron is from 2:1 to 1:2; preferably from 3:1 to 1:1; preferably from 2:1 to 1:1; a weight ratio of IPBC to DCOIT is from 7:1 to 4:1; preferably from 8:1 to 5:1; preferably from 7:1 to 5:1; preferably from 6:1 to 5:1.

In some embodiments of the invention in which the antimicrobial composition comprises IPBC, fluometuron and DIMTS, a weight ratio of IPBC to DIMTS is from 2:1 to 1:2; preferably from 3:1 to 1:1; preferably from 2:1 to 1:1; a weight ratio of IPBC to DIMTS is from 7:1 to 4:1; preferably from 8:1 to 5:1; preferably from 7:1 to 5:1; preferably from 6:1 to 5:1.

In some embodiments of the invention in which the antimicrobial composition comprises fluometuron and ZPT, a weight ratio of fluometuron to ZPT is from 10:1 to 1:12, preferably from 8:1 to 1:12, preferably from 10:1 to 1:10; preferably from 8:1 to 1:10, preferably from 7:1 to 1:10; preferably from 6:1 to 1:10.

In some embodiments of the invention in which the antimicrobial composition comprises fluometuron and TBZ, a weight ratio of fluometuron to TBZ is from 10:1 to 1:12, preferably from 8:1 to 1:12, preferably from 10:1 to 1:10; preferably from 8:1 to 1:10, preferably from 7:1 to 1:10; preferably from 6:1 to 1:10.

In some embodiments of the invention in which the antimicrobial composition comprises fluometuron and DMITS, a weight ratio of fluometuron to DMITS is from 10:1 to 1:12, preferably from 8:1 to 1:12, preferably from 10:1 to 1:10; preferably from 8:1 to 1:10, preferably from 7:1 to 1:10; preferably from 6:1 to 1:10.

In some embodiments of the invention, the antimicrobial combinations of this invention are incorporated into liquid compositions, especially dispersions of polymers in aqueous media. The biocide combinations are particularly useful in preservation of building materials, e.g., adhesives, caulk, joint compound, sealant, wallboard, etc), paints, coatings, polymers, plastics, synthetic and natural rubber, paper products, fiberglass sheets, insulation, exterior insulating finishing systems, roofing and flooring felts, building plasters, wood products and wood-plastic composites. In some embodiments of the invention, the antimicrobial compositions are latex paints or other liquid coating compositions containing the biocide combinations disclosed herein. The biocide combinations are useful for preservation of the dry film coating resulting after application of a paint or other liquid coating composition. In some embodiments, the antimicrobial composition is an acrylic latex paint comprising one or more of the biocide combinations disclosed herein, or the dry film coating resulting from application of the paint to a surface.

Typically, the amount of the biocide combinations of the present invention to control the growth of microorganisms is from 100 ppm to 10,000 ppm active ingredient. In some embodiments of the invention, the active ingredients of the composition are present in an amount of at least 300 ppm, preferably at least 500 ppm, preferably at least 600 ppm, preferably at least 700 ppm. In some embodiments, the active ingredients of the composition are present in an amount of no more than 8,000 ppm, preferably no more than 6,000 ppm, preferably no more than 5,000 ppm, preferably no more than 4,000 ppm, preferably no more than 3,000 ppm, preferably no more than 2500 ppm, preferably no more than 2,000 ppm, preferably no more than 1,800 ppm, preferably no more than 1,600 ppm. Concentrations mentioned above are in a liquid composition containing the biocide combinations; biocide levels in the dry film coating will be higher.

The present invention also encompasses a method for preventing microbial growth in building materials, especially in dry film coatings, by incorporating any of the claimed biocide combinations into the materials.

Fluometuron may be combined with more than one of IPBC, DCOIT, OIT, ZPT, DIMTS and TBZ to produce synergistic ternary or higher combinations not disclosed elsewhere herein.

EXAMPLES

Sample Preparation:

Samples of white acrylic latex paint free of biocides were prepared in 50 ml aliquots. Each biocide was post added to give the necessary active ingredient concentration in the paint. The total biocides concentrations tested were 750, 1500, 2500 and 5000 ppm. After biocides addition, each sample was hand mixed for a minimum of 30 sec, followed by a 3 min run on the paint shaker (RED DEVIL). Each of the paint samples as well as a control sample (containing no biocide) were used to prepare films on black plastic-vinyl chloride/acetate copolymer panels (LENETA, Mahwah, N.J.) using a 3 mil bird bar applicator. The panels were thoroughly dried for 5 days avoiding direct exposure to sunlight. Square discs (15 mm$^2$) were cut out from each panel and were used as the substrate for fungal and algal efficacy tests. This sample size allowed for an agar border when the sample disc was placed into the well of the test plate.

Test Conditions:

The appropriate media (BOLD'S 3N for Chlorophytes, BG-11 for Cyanobacteria, and PDA for fungi) were used to support microbial growth. The test plates were maintained at room temp (25° C.-26° C.), in a cycled light-dark environment, for 3 weeks for algae. Plates for fungal challenge tests were maintained at 30C for three weeks. At the end of incubation period the samples were scored for percent area covered by visible microbial growth.

Algal Inoculum

| Organisms | abbreviation | Type | Medium for testing |
|---|---|---|---|
| Gleocapsa sp. | Gs | ATCC 29159 | Unicellular, Colonial Cyanobacteria | BG-11 |
| Oscillatoria sp. | Os | ATCC 29135 | Filamentous Cyanobacteria | BG-11 |
| Nostoc commune | Nc | CCAP 1453/29 | Unicellular, Cenobial Chlorophyte | Bold |
| Trentepohlia aurea + Trentepohlia odorata | Ta + To | UTEX LB 429 + CCAP 483/4 | Filamentous Chlorophyte | Bold |
| Chlorella sp. + Chlorella kessleri | Cs + Ck | ATCC 30582 + ATCC 11468 | Unicellular Chlorophyte | Bold |
| Calothrix parientina | Cp | UTEX LB 1952 | Filamentous Cyanobacteria | Bold |

Fungal Inoculum

| Organisms | abbreviation | ATCC# | Medium for Growth and Testing |
|---|---|---|---|
| Aspergillus niger | An | 9642 | PDA |
| Penicillium funiculosum | Pf | 11797 | PDA |
| Cladosporium herbarum | Ch | 11281 | PDA |
| Aureobasidium pullulans | Ap | 9348 | PDA |
| Trichoderma viride | Tv | 32630 | PDA |
| Alternaria alternata | Aa | 20084 | PDA |
| Stachybotris chartarum | Sc | 208877 | PDA |

Algal Efficacy Testing—Modified ASTM 5589

ASTM 5589 is a standard accelerated test method for determining resistance of various coatings (including paints) to algal defacement. To accommodate for high-throughput screening, this method was scaled down from petri plates to 12-well plates. A single coupon was placed with a pair of sterile forceps at the center of the agar plug (on top) with the painted surface facing upwards. Each well was inoculated with 150 µl of organism ($1\times10^8$ cfu/ml) making sure that the whole surface (paint film as well as the agar surrounding it) was evenly covered. The plates were incubated at room temp (25° C.-26° C.) with cyclic exposure to light (OTT-Lite model #OTL4012P, 40 Watt, 26 KLumen) and dark phases, for a period of three weeks. The total area covered was evaluated at the end of each week according to percent area covered in 5% increments. While rating the plates, notations were made for zones of inhibition.

Fungal Efficacy Testing—Modified ASTM 5590

ASTM 5590 is a standard accelerated test method for determining resistance of various coatings (including paints) to fungal defacement. To accommodate for high-throughput screening, this method was scaled down from petri plates to 12-well plates. To set up the test, an agar plug was placed at the bottom of each well of the sterile 12-well plate. A single coupon was placed with a pair of sterile forceps at the center of the agar plug (on top) with the painted surface facing upwards. Each well was inoculated with 150 µl of organism ($1\times10^6$ cfu/ml) making sure that the whole surface (paint film as well as the agar surrounding it) was evenly covered. The plates were incubated at 30° C. in presence of moisture, for a period of three weeks. The total percent area covered was evaluated and recorded at the end of each week after the $2^{nd}$ week and recorded in increments of 5%.

Synergy Index (SI)

The SI is calculated based on F. C. Kull et. Al. method (Applied Microbiology, Vol. 9 (1961). In this study, SI was calculated based on the following formula with the minimum inhibitory concentration chosen based on the percent inhibitory exhibited by the individual biocide against each microorganisms tested.

$$SI = Qa/QA + Qb/QB + Qc/QC + \ldots$$

Qa=the concentration of Biocide A in the blend
QA=The concentration of Biocide A as the only biocide
Qb=The concentration of Biocide B in the blend
QB=The concentration of Biocide B as the only biocide
Qc=The concentration of Biocide C in the blend
QC=The concentration of Biocide C as the only biocide SI value of <1 in the formula indicates a synergism of the blended biocides exists.

Example 1

This study was performed to investigate the performance of IPBC and Fluometuron blends with weight ratios of IPBC to Fluometuron (Fluo) from 4:1 to 1:1. These blends exhibited very good synergism against a wide spectrum of fungi and algae. Each mixture tested displayed synergy against at least one organism at all ratios of IPBC to Fluometuron tested. Results after three weeks of exposure are presented in Table 1 for algae and Table 2 for fungi.

TABLE 1

| (Algae) | | | | | | |
|---|---|---|---|---|---|---|
| | Cs + Ck | Nc | Cp | Ta + To | Gs | Os |
| 1IPBC:1Fluo | | | | | | |
| Total conc, ppm | 1500 | 750 | 1500 | 2500 | 750 | 750 |
| % inhibition | 95 | 97.5 | 97.5 | 87.5 | 100 | 95 |
| SI | 1.5 | 0.75 | 1.3 | 2.17 | 1 | 0.65 |
| 2IPBC:1 Fluo | | | | | | |
| Total conc, ppm | 1500 | 750 | 1500 | 2500 | 750 | 750 |
| % inhibition | 95 | 100 | 95 | 92.5 | 100 | 100 |
| SI | 1.33 | 0.67 | 1.07 | 1.78 | 1 | 0.53 |
| 3IPBC:1Fluo | | | | | | |
| Total conc, ppm | 1500 | 750 | 1500 | 2500 | 750 | 750 |
| % inhibition | 100 | 95 | 100 | 92.5 | 95 | 97.5 |
| SI | 1.25 | 0.63 | 0.95 | 1.58 | 1 | 0.48 |
| 4IPBC:1Fluo | | | | | | |
| Total conc, ppm | 2500 | 750 | 1500 | 1500 | 750 | 750 |
| % inhibition | 97.5 | 100 | 100 | 90 | 100 | 95 |
| SI | 2 | 0.6 | 0.88 | 0.88 | 1 | 0.44 |
| IPBC | | | | | | |
| Total conc, ppm | 1500 | 1500 | 2500 | 2500 | 750 | 750 |
| % inhibition | 97.5 | 87.5 | 97.5 | 85 | 95 | 70 |
| Fluometuron | | | | | | |
| Total conc, ppm | 750 | 750 | 750 | 750 | 750 | 1500 |
| % inhibition | 100 | 100 | 100 | 95 | 95 | 95 |

TABLE 2

| (Fungi) | | | | | | |
|---|---|---|---|---|---|---|
| | Ap | Ch | Pf | An | Aa | Tv |
| 1IPBC:1Fluo | | | | | | |
| Total conc, ppm | 1500 | 750 | 1500 | 750 | 750 | 750 |
| % inhibition | 97.5 | 100 | 100 | 100 | 100 | 87.5 |
| SI | 0.6 | 0.65 | 1.3 | 0.65 | 0.65 | 0.75 |
| 2IPBC:1 Fluo | | | | | | |
| Total conc, ppm | 1500 | 750 | 1500 | 750 | 750 | 750 |
| % inhibition | 100 | 100 | 100 | 100 | 97.5 | 100 |
| SI | 0.6 | 0.77 | 1.53 | 0.77 | 0.77 | 0.83 |
| 3IPBC:1Fluo | | | | | | |
| Total conc, ppm | 750 | 750 | 1500 | 750 | 750 | 750 |
| % inhibition | 100 | 97.5 | 100 | 100 | 100 | 97.5 |
| SI | 0.3 | 0.83 | 1.65 | 0.83 | 0.83 | 0.88 |
| 4IPBC:1Fluo | | | | | | |
| Total conc, ppm | 750 | 750 | 1500 | 750 | 750 | 750 |
| % inhibition | 100 | 100 | 100 | 97.5 | 100 | 95 |
| SI | 0.3 | 0.86 | 1.72 | 0.86 | 0.86 | 0.9 |
| IPBC | | | | | | |
| Total conc, ppm | 2500 | 750 | 750 | 2500 | 750 | 750 |
| % inhibition | 97.5 | 75 | 97.5 | 87.5 | 97.5 | 90 |
| Fluometuron | | | | | | |
| Total conc, ppm | 2500 | 2500 | 2500 | 2500 | 2500 | 1500 |
| % inhibition | 97.5 | 90 | 97.5 | 35 | 25 | 57.5 |

Example 2

This study was performed to investigate the performance of IPBC and Fluometuron blends with weight ratios of IPBC to Fluometuron (Fluo) from 1:2 to 1:3. These blends exhibited very good synergism against a wide spectrum of fungi and algae. Each mixture tested displayed synergy against at least one organism at all ratios of IPBC to Fluometuron tested. Results after three weeks of exposure are presented in Table 3 for algae and Table 4 for fungi.

TABLE 3

| (Algae) | | | | | | |
|---|---|---|---|---|---|---|
| | Cs + Ck | Nc | Cp | Ta + To | Gs | Os |
| 1IPBC:3Fluo | | | | | | |
| Total conc, ppm | 1500 | 750 | 750 | 750 | 2500 | 2500 |
| % inhibition | 95 | 97.5 | 95 | 85 | 52.50 | 72.5 |
| SI | 0.3 | 0.83 | 0.82 | 0.88 | 1 | 2.33 |
| 1IPBC:2Fluo | | | | | | |
| Total conc, ppm | 2500 | 750 | 750 | 750 | 2500 | 750 |
| % inhibition | 90 | 95 | 90 | 87.5 | 50 | 65 |
| SI | 0.5 | 0.77 | 0.77 | 0.83 | 1 | 0.37 |
| IPBC | | | | | | |
| Total conc, ppm | 5000 | 2500 | 2500 | 1500 | 2500 | 1500 |
| % inhibition | 90 | 90 | 90 | 82.5 | 50 | 62.5 |
| Fluometuron | | | | | | |
| Total conc, ppm | 5000.00 | 750 | 750 | 750 | 2500 | 2500 |
| % inhibition | 90.00 | 90 | 95 | 82.5 | 42.5 | 62.5 |

TABLE 4

(Fungi)

|  | Ap | Ch | Pf | An | Aa | Tv |
|---|---|---|---|---|---|---|
| 1IPBC:3Fluo |  |  |  |  |  |  |
| Total conc, ppm | 750 | 750 | 750 | 750 | 1500 | 750 |
| % inhibition | 70 | 82.5 | 72.5 | 90 | 62.5 | 72.5 |
| SI | 0.79 | 0.41 | 0.24 | 0.24 | 0.3 | 0.24 |
| 1IPBC:2Fluo |  |  |  |  |  |  |
| Total conc, ppm | 750 | 750 | 750 | 750 | 750 | 750 |
| % inhibition | 95 | 87.5 | 82.5 | 85 | 82.5 | 82.5 |
| SI | 0.72 | 0.38 | 0.27 | 0.27 | 0.15 | 0.27 |
| IPBC |  |  |  |  |  |  |
| Total conc, ppm | 750 | 1500 | 1500 | 1500 | 5000 | 1500 |
| % inhibition | 60 | 75 | 60 | 80 | 50 | 72.5 |
| Fluometuron |  |  |  |  |  |  |
| Total conc, ppm | 5000 | 5000 | 5000 | 5000 | 5000 | 5000 |
| % inhibition | 0 | 0 | 27.5 | 0 | 0 | 0 |

Example 3

Three-Component Biocide Mixtures

These mixtures also displayed synergy against a variety of organisms at each weight ratio tested, as described in Tables 5 and 6.

TABLE 5

(Algae)

|  | Cs + Ck | Nc | Cp | Ta + To | Gs | Os |
|---|---|---|---|---|---|---|
| 6IPBC:3Fluo:1DCOIT |  |  |  |  |  |  |
| Total conc, ppm | 750 | 750 | 1500 | 2500 | 1500 | 1500 |
| % inhibition | 75 | 97.5 | 87.5 | 90 | 67.5 | 80 |
| SI | 0.32 | 0.58 | 0.88 | 1.27 | 0.75 | 0.65 |
| 5IPBC:5Fluo:1DCOIT |  |  |  |  |  |  |
| Total conc, ppm | 1500 | 750 | 2500 | 1500 | 1500 | 2500 |
| % inhibition | 95 | 85 | 97.5 | 95 | 80 | 95 |
| SI | 0.64 | 0.68 | 0.83 | 0.82 | 0.65 | 0.98 |
| 6IPBC:3Fluo:1DIMTS |  |  |  |  |  |  |
| Total conc, ppm | 1500 | 1500 | 1500 | 1500 | 1500 | 750 |
| % inhibition | 70 | 75 | 77.5 | 82.5 | 77.5 | 95 |
| SI | 0.54 | 0.99 | 0.88 | 0.72 | 0.75 | 0.28 |
| 5IPBC:5Fluo:1DIMTS |  |  |  |  |  |  |
| Total conc, ppm | 750 | 750 | 1500 | 1500 | 750 | 750 |
| % inhibition | 80 | 100 | 95 | 90 | 75 | 97.5 |
| SI | 0.3 | 0.6 | 1.14 | 0.78 | 0.32 | 0.25 |
| IPBC |  |  |  |  |  |  |
| Total conc, ppm | 2500 | 2500 | 5000 | 2500 | 1500 | 2500 |
| % inhibition | 70 | 80 | 80 | 72.5 | 80 | 77.5 |
| Fluometuron |  |  |  |  |  |  |
| Total conc, ppm | 2500 | 750 | 750 | 1500 | 5000 | 5000 |
| % inhibition | 80 | 85 | 90 | 62.5 | 67.5 | 82.5 |
| DCOIT |  |  |  |  |  |  |
| Total conc, ppm | 1500 | 750 | 1500 | 1500 | 2500 | 750 |
| % inhibition | 70 | 82.5 | 75 | 72.5 | 77.5 | 80 |
| DIMTS |  |  |  |  |  |  |
| Total conc, ppm | 2500 | 5000 | 1500 | 2500 | 2500 | 1500 |
| % inhibition | 70 | 80 | 85 | 62.5 | 80 | 80 |

TABLE 6

(Fungi)

|  | Ap | Ch | Pf | An | Aa | Tv | Sc |
|---|---|---|---|---|---|---|---|
| 6IPBC:3Fluo:1DCOIT |  |  |  |  |  |  |  |
| Total conc, ppm | 750 | 1500 | 750 | 750 | 2500 | 750 | 1500 |
| % inhibition | 82.5 | 100 | 90 | 750 | 95 | 100 | 85 |
| SI | 0.3 | 0.57 | 0.3 | 0.24 | 0.65 | 0.42 | 0.48 |
| 5IPBC:5Fluo:1DCOIT |  |  |  |  |  |  |  |
| Total conc, ppm | 750 | 750 | 750 | 750 | 750 | 750 | 1500 |
| % inhibition | 97.5 | 72.5 | 82.5 | 100 | 100 | 97.5 | 50 |
| SI | 0.3 | 0.29 | 0.3 | 0.22 | 0.22 | 0.39 | 0.44 |
| 6IPBC:3Fluo:1DIMTS |  |  |  |  |  |  |  |
| Total conc, ppm | 750 | 750 | 1500 | 1500 | 2500 | 750 | 750 |
| % inhibition | 97.5 | 100 | 77.5 | 100 | 90 | 95 | 72.5 |
| SI | 0.39 | 0.37 | 0.64 | 0.65 | 0.63 | 0.42 | 0.33 |
| 5IPBC:5Fluo:1DIMTS |  |  |  |  |  |  |  |
| Total conc, ppm | 750 | 2500 | 750 | 750 | 2500 | 750 | 1500 |
| % inhibition | 97.5 | 82.5 | 92.5 | 87.5 | 90 | 80 | 75 |
| SI | 0.39 | 1.21 | 0.32 | 0.3 | 0.71 | 0.39 | 0.59 |
| IPBC |  |  |  |  |  |  |  |
| Total conc, ppm | 2500 | 2500 | 2500 | 2500 | 5000 | 1500 | 2500 |
| % inhibition | 87.5 | 80 | 70 | 75 | 100 | 62.5 | 82.5 |
| Fluometuron |  |  |  |  |  |  |  |
| Total conc, ppm | 2500 | 2500 | 2500 | 5000 | 2500 | 2500 | 5000 |
| % inhibition | 80 | 72.5 | 70 | 75 | 82.5 | 72.5 | 65 |
| DCOIT |  |  |  |  |  |  |  |
| Total conc, ppm | 2500 | 5000 | 2500 | 5000 | 5000 | 2500 | 5000 |
| % inhibition | 77.5 | 67.5 | 82.5 | 75 | 87.5 | 60 | 32.5 |
| DIMTS |  |  |  |  |  |  |  |
| Total conc, ppm | 2500 | 750 | 1500 | 750 | 2500 | 750 | 750 |
| % inhibition | 77.5 | 72.5 | 82.5 | 75 | 77.5 | 90 | 50 |

Example 4

Further Biocide Mixtures

The organisms and their growth media are as stated in the earlier examples.

Sample Preparation:

A single or blend of biocides was post added into white acrylic latex paint free of biocides to give a maximum total active ingredient/s concentration tested. This paint was then diluted with a biocide free acrylic latex paint at concentrations range of 75 to 12.5% w/w to give desired concentrations for the testing. Depending on the type of biocide blends tested, the total biocides concentrations varies from 200 to 5000 ppm. After biocides addition or dilution each sample was hand mixed for at least a minute until uniformity is achieved. Each of the paint samples as well as a control sample (containing no biocide) were used to prepare films on black plastic-vinyl chloride/acetate copolymer panels (LENETA, Mahwah, N.J.) using a 3 mil bird bar applicator. The panels were thoroughly dried for at least 2 days avoiding direct exposure to sunlight. Square discs (0.5 inch$^2$, 13 mm$^2$) were cut out from each panel and were used as the substrate for fungal and algal efficacy tests. This sample size allowed for an agar border when the sample disc was placed into the well of the test plate. Each sample was tested in duplicate Test Conditions:

The appropriate media (BOLD'S 3N for Chlorophytes, BG-11 for Cyanobacteria, and PDA for fungi) were used to support microbial growth. The test plates were maintained at room temp (25° C.-26° C.), in a cycled light-dark environment, for four weeks for algae. Plates for fungal challenge tests were maintained at 30 C for four weeks. At the end of the incubation period the samples were scored for percent area covered by visible microbial growth.

Algal Efficacy Testing—Modified ASTM 5589

ASTM 5589 is a standard accelerated test method for determining resistance of various coatings (including paints) to algal defacement. To accommodate for high-throughput screening, this method was scaled down from petri plates to 6-well plates. A single coupon was placed with a pair of sterile forceps at the center of the agar plug (on top) with the painted surface facing upwards. Algal inoculums were prepared by mixing equal concentrations ($1\times10^6$ cfu/ml) and equal volumes (depending on number of samples to be inoculated) of like growing organisms. In this study, *Gloeocapsa* sp. and *Oscillatoria* sp. were a mix of cyanobacteria grown on BG-11 media. *Chlorella* sp., *Chlorella kessleri*, and *Nostoc commune* are unicellular chlorphytes that were mixed and grown on Bold media. *Trentepohlia aurea*, *Trentepohlia odorata*, and *Calotrix parientina* are filamentous algae that were mixed and grown on Bold media. Each well was inoculated with 400 μl of organism mixture ($1\times10^6$ cfu/ml) making sure that the whole surface (paint film as well as the agar surrounding it) was evenly covered. The plates were incubated at room temp (25° C.-26° C.) with cyclic exposure to light (OTT-Lite model #OTL4012P, 40 Watt, 26 KLumen) and dark phases, for a period of four weeks. The total area covered was evaluated at the end of each week according to percent area covered in 5% increments. While rating the plates, notations were made for zones of inhibition.

Fungal Efficacy Testing—Modified ASTM 5590

ASTM 5590 is a standard accelerated test method for determining resistance of various coatings (including paints) to fungal defacement. To accommodate for high-throughput screening, this method was scaled down from petri plates to 6-well plates. To set up the test, an agar plug was placed at the bottom of each well of the sterile 6-well plate. A single coupon was placed with a pair of sterile forceps at the center of the agar plug (on top) with the painted surface facing upwards. Fungal inoculums were prepared by mixing equal concentrations ($1\times10^6$ cfu/ml) and equal volumes (depending on number of samples to be tested) of like growing organisms. *Cladosporium herbarum* was mixed with *Aureobasidium pullulans*. *Aspergillus niger* was mixed with *Penicillium funiculosum*. *Alternaria alternata* was mixed with *Trichoderma viride*. Each well was inoculated with 400 μl of organism mixture ($1\times10^6$ cfu/ml) making sure that the whole surface (paint film as well as the agar surrounding it) was evenly covered. The plates were incubated at 30° C. in presence of moisture, for a period of four weeks. The total percent area covered was evaluated and recorded at the end of each week after the $2^{nd}$ week and recorded in increments of 5%. The results are presented in Tables 7-11 below.

TABLE 7

Fluometuron: DCOIT synergy study

|  | Aa + Ap | Cp + To + Ta | Cs + Ck + Nc | Gs + Os |
|---|---|---|---|---|
| 2.2Fluo: 1DCOIT |  |  |  |  |
| Total conc, ppm | 2737.5 | 912.5 | 2737.5 | 912.5 |
| % inhibition | 100 | 100 | 100 | 100 |
| SI | 1.4 | 1.0 | 3.0 | 3.0 |
| 2.9Fluo: 1DCOIT |  |  |  |  |
| Total conc, ppm | 2521.9 | 1681.5 | 1681.25 | 420.3 |
| % inhibition | 100 | 100 | 100 | 100 |
| SI | 1.1 | 1.8 | 1.8 | 1.4 |
| 4.3Fluo: 1DCOIT |  |  |  |  |
| Total conc, ppm | 3075 | 3075 | 3075 | 384.37 |
| % inhibition | 100 | 100 | 100 | 100 |
| SI | 1.2 | 3.0 | 3.0 | 1.2 |
| 1.1Fluo: 1DCOIT |  |  |  |  |
| Total conc, ppm | 1200 | 600 | 600 | 1200 |
| % inhibition | 100 | 100 | 100 | 100 |
| SI | <0.8 | 0.8 | 0.8 | 4.0 |
| 1Fluo: 1.8DCOIT |  |  |  |  |
| Total conc, ppm | 1325.3 | 1331.25 | 1331.25 | 887.5 |
| % inhibition | 100 | 100 | 100 | 100 |
| SI | 1.1 | 1.9 | 1.9 | 3.0 |
| 1Fluo: 10DCOIT |  |  |  |  |
| Total conc, ppm | 1265 | 632.5 | 632.5 | 1265 |
| % inhibition | 1.4 | 100 | 100 | 100 |
| SI |  | 1.0 | 1.9 | 4.4 |
| Fluometuron |  |  |  |  |
| Total conc, ppm | 5000 | 1250 | 1250 | 312.5 |
| % inhibition | 0 | 100 | 100 | 100 |
| DCOIT |  |  |  |  |
| Total conc, ppm | 862.5 | 575 | 575 | 287.5 |
| % inhibition | 100 | 100 | 100 | 100 |

Note:
Since maximum concentration of Fluometuron tested against fungi is 5000 ppm, this concentration is used to calculate the estimated SI. A correction by using less than sign (<) is included only to the relevant data, SI < 1.
NE = no end point at the concentration tested.

TABLE 8

Fluometuron:OIT Synergy study

|  | Aa + Ap | An + Pf | Ch + Tv | Cp + To + Ta | Cs + Ck + Nc | Gs + Os |
|---|---|---|---|---|---|---|
| 1Fluo: 1OIT |  |  |  |  |  |  |
| Total conc, ppm | 3000 | 750 | 750 | 2250 | 1500 | 2250 |
| % inhibition | 100 | 100 | 100 | 100 | 100 | 100 |
| SI | 1.4 | <0.9 | 0.9 | 1.7 | 1.2 | 4.4 |
| 1Fluo:2OIT |  |  |  |  |  |  |
| Total conc, ppm | 1500 | 1500 | 1500 | 3000 | 2250 | 1500 |
| % inhibition | 100 | 100 | 100 | 100 | 100 | 100 |
| SI | <0.9 | 2.3 | 2.3 | 2.3 | 1.7 | 2.3 |
| 1Fluo:3OIT |  |  |  |  |  |  |
| Total conc, ppm | 2250 | 1500 | 1500 | 3000 | 3000 | 1500 |
| % inhibition | 100 | 100 | 100 | 100 | 100 | 100 |
| SI | 1.4 | 2.6 | 2.6 | 2.3 | 2.3 | 2.0 |
| 1Fluo:5OIT |  |  |  |  |  |  |
| Total conc, ppm | 2700 | 2700 | 2700 | 3600 | 2500 | 2400 |
| % inhibition | 100 | 100 | 100 | 100 | 100 | 100 |
| SI | 1.8 | 5.1 | 5.1 | 1.9 | 1.9 | 2.8 |
| 3Fluo:1OIT |  |  |  |  |  |  |
| Total conc, ppm |  | 2400 | 2400 | 1800 | 1800 | 1200 |
| % inhibition |  | 100 | 100 | 100 | 100 | 100 |
| SI | NE | 1.7 | 1.7 | 1.4 | 1.4 | 6.3 |

TABLE 8-continued

Fluometuron:OIT Synergy study

| | Aa + Ap | An + Pf | Ch + Tv | Cp + To + Ta | Cs + Ck + Nc | Gs + Os |
|---|---|---|---|---|---|---|
| 2Fluo:1OIT | | | | | | |
| Total conc, ppm | | 1350 | 1350 | 1975 | 1350 | 1350 |
| % inhibition | | 100 | 100 | 100 | 100 | 100 |
| SI | NE | 1.2 | 1.2 | 1.6 | 1.1 | 3.2 |
| Fluometuron | | | | | | |
| Total conc, ppm | 5000 | 5000 | 5000 | 1250 | 1250 | 312.5 |
| % inhibition | 0 | 0 | 0 | 100 | 100 | 100 |
| OIT | | | | | | |
| Total conc, ppm | 1350 | 450 | 450 | 1350 | 1350 | 1350 |
| % inhibition | 100 | 100 | 50 | 95 | 100 | 100 |

TABLE 9

Fluometuron: ZPT synergy study

| | Aa + Ap | An + Pf | Cp + To + Ta | Cs + Ck + Nc | Gs + Os |
|---|---|---|---|---|---|
| 1Fluo: 1ZPT | | | | | |
| Total conc, ppm | NE | 750 | 750 | 1500 | 750 |
| % inhibition | | 100 | 100 | 100 | 100 |
| SI | | <0.4 | 0.9 | 1.2 | 1.8 |
| 1Fluo: 3ZPT | | | | | |
| Total conc, ppm | 1500 | 1500 | 750 | 1500 | 750 |
| % inhibition | 100 | 100 | 100 | 100 | 100 |
| SI | <0.5 | 1.0 | 1.1 | 1.2 | 1.5 |
| 1Fluo: 5ZPT | | | | | |
| Total conc, ppm | 1500 | 1500 | 750 | 750 | 750 |
| % inhibition | 100 | 100 | 100 | 100 | 100 |
| SI | <0.6 | 1.1 | 1.1 | 0.6 | 1.4 |
| 1Fluo: 10ZPT | | | | | |
| Total conc, ppm | 2750 | 1375 | 687.5 | 687.5 | 687.5 |
| % inhibition | 100 | 100 | 100 | 100 | 100 |
| SI | 1.1 | 1.0 | 1.1 | 0.6 | 1.2 |
| 6Fluo: 1ZPT | | | | | |
| Total conc, ppm | NE | 2800 | 600 | 725 | 725 |
| % inhibition | | 100 | 100 | 100 | 100 |
| SI | | <0.8 | 0.2 | 0.6 | 2.2 |
| 4Fluo: 1ZPT | | | | | |
| Total conc, ppm | NE | 2437.5 | 1625 | 1625 | 787.5 |
| % inhibition | | 100 | 100 | 100 | 100 |
| SI | | <0.8 | 1.6 | 1.3 | 2.3 |
| 2Fluo: 1ZPT | | | | | |
| Total conc, ppm | 750 | 2250 | 2250 | 1500 | 750 |
| % inhibition | 100 | 100 | 100 | 100 | 100 |
| SI | <0.2 | <0.9 | 2.4 | 1.2 | 2.0 |
| Fluometuron | | | | | |
| Total conc, ppm | 5000 | 5000 | 1250 | 1250 | 312.5 |
| % inhibition | 0 | 0 | 100 | 100 | 100 |
| ZPT | | | | | |
| Total conc, ppm | 2500 | 1250 | 625 | 1250 | 625 |
| % inhibition | 100 | 100 | 100 | 100 | 100 |

TABLE 10

Fluometuron:Thiabendazole (TBZ) synergy study

| | Aa + Ap | An + Pf | Ch + Tv | Cp + To + Ta | Cs + Ck + Nc | Gs + Os |
|---|---|---|---|---|---|---|
| 1Fluo:1TBZ | | | | | | |
| Total conc, ppm | 4000 | 3000 | 500 | 2000 | 4000 | 2000 |
| % inhibition | 80 | 90 | 100 | 95 | 100 | 100 |
| SI | <0.9 | 2.7 | <0.5 | 0.9 | 2.4 | 3.4 |
| 1Fluo:3TBZ | | | | | | |
| Total conc, ppm | 4000 | 2000 | 500 | 500 | 4000 | 1000 |
| % inhibition | 100 | 90 | 100 | 100 | 100 | 100 |
| SI | 1.0 | 2.5 | <0.6 | 0.2 | 2.4 | 1.0 |
| 1Fluo:5TBZ | | | | | | |
| Total conc, ppm | 3000 | 2000 | 500 | NE | NE | 3000 |
| % inhibition | 100 | 90 | 100 | | | 100 |
| SI | <0.8 | 2.7 | <0.7 | | | 2.1 |
| 1Fluo:7TBZ | | | | | | |
| Total conc, ppm | 4000 | 4000 | 501 | 4000 | NE | NE |
| % inhibition | 100 | 90 | 100 | 100 | | |
| SI | 1.0 | 5.7 | <0.7 | 1.1 | | |
| 1Fluo:10TBZ | | | | | | |
| Total conc, ppm | NE | 2887 | 517.25 | 3850 | 3850 | NE |
| % inhibition | | 90 | 100 | 100 | 100 | |
| SI | | 4.3 | <0.8 | 1.0 | 1.7 | |
| 6Fluo:1TBZ | | | | | | |
| Total conc, ppm | NE | NE | 1750 | 1750 | 1750 | 2625 |
| % inhibition | | | 100 | 100 | 100 | 100 |
| SI | | | <0.7 | 1.3 | 1.3 | 7.3 |
| 4Fluo: 1TBZ | | | | | | |
| Total conc, ppm | 2812.5 | NE | 1875 | 458 | 1875 | 1875 |
| % inhibition | 80 | | 100 | 100 | 100 | 100 |
| SI | <0.7 | | <0.9 | 0.3 | 1.4 | 4.9 |
| 2Fluo:1TBZ | | | | | | |
| Total conc, ppm | 2812.5 | NE | 468.75 | 468.75 | 3750 | 1875 |
| % inhibition | 80 | | 100 | 100 | 100 | 100 |
| SI | <0.6 | | <0.3 | 0.3 | 2.5 | 4.1 |
| Fluometuron | | | | | | |
| Total conc, ppm | 5000 | 5000 | 5000 | 1250 | 1250 | 312.5 |
| % inhibition | 0 | 0 | 0 | 100 | 100 | 100 |
| TBZ | | | | | | |
| Total conc, ppm | 3750 | 625 | 2500 | 1875 | 1250 | 1875 |
| % inhibition | 80 | 100 | 50 | 95 | 100 | 100 |

TABLE 11

Fluometuron and DMITS synergy study

| | Aa + Ap | An + Pf | Cp + To + Ta | Cs + Ck + Nc | Gs + Os |
|---|---|---|---|---|---|
| 1Fluo: 1DMITS | | | | | |
| Total conc, ppm | 2250 | 750 | 750 | 2250 | 750 |
| % inhibition | 100 | 100 | 95 | 100 | 100 |
| SI | 1.1 | <0.7 | 0.5 | 1.8 | 1.4 |
| 1Fluo: 3DMITS | | | | | |
| Total conc, ppm | 1500 | 750 | 1500 | 1500 | NE |
| % inhibition | 100 | 100 | 100 | 100 | |
| SI | 1.2 | <0.9 | 0.9 | 1.2 | |
| 1Fluo: 5DMITS | | | | | |
| Total conc, ppm | 1500 | 1500 | 1500 | 750 | NE |
| % inhibition | 100 | 100 | 100 | 100 | |
| SI | 1.1 | 2.1 | 0.9 | 0.6 | |

TABLE 11-continued

Fluometuron and DMITS synergy study

|  | Aa + Ap | An + Pf | Cp + To + Ta | Cs + Ck + Nc | Gs + Os |
|---|---|---|---|---|---|
| 1Fluo: 7DMITS |  |  |  |  |  |
| Total conc, ppm | 750 | 750 | 750 | 750 | 1500 |
| % inhibition | 100 | 100 | 100 | 100 | 100 |
| SI | <0.5 | 1.1 | 0.4 | 0.6 | 1.3 |
| 1Fluo: 10DMITS |  |  |  |  |  |
| Total conc, ppm | 1500 | 750 | 750 | 750 | 3000 |
| % inhibition | 100 | 100 | 100 | 100 | 100 |
| SI | 1.1 | 1.1 | 0.4 | 0.6 | 2.4 |
| 6Fluo: 1DMITS |  |  |  |  |  |
| Total conc, ppm | NE | 1400 | NE | 725 | 1400 |
| % inhibition |  | 100 |  | 100 | 100 |
| SI |  | <0.6 |  | 0.6 | 3.9 |
| 4Fluo: 1DMITS |  |  |  |  |  |
| Total conc, ppm | NE | 812.5 | 2250 | 2250 | 1625 |
| % inhibition |  | 100 | 95 | 100 | 100 |
| SI |  | <0.4 | 1.7 | 1.8 | 4.3 |
| 2Fluo: 1DMITS |  |  |  |  |  |
| Total conc, ppm | NE | 750 | 2250 | 750 | 750 |
| % inhibition |  | 100 | 100 | 100 | 100 |
| SI |  | <0.5 | 1.6 | 0.6 | 1.7 |
| Fluometuron |  |  |  |  |  |
| Total conc, ppm | 5000 | 5000 | 1250 | 1250 | 312.5 |
| % inhibition | 0 | 0 | 100 | 100 | 100 |
| DMITS |  |  |  |  |  |
| Total conc, ppm | 1250 | 1250 | 1875 | 1250 | 1875 |
| % inhibition | 100 | 100 | 95 | 100 | 100 |

The invention claimed is:

1. A synergistic antimicrobial composition comprising: (a) 3-iodo-2-propynyl-butylcarbamate; and (b) fluometuron; wherein a weight ratio of 3-iodo-2-propynyl-butylcarbamate to fluometuron is from 4:1 to 1:3.

2. The synergistic antimicrobial composition of claim 1 which is an acrylic latex paint.

3. The synergistic antimicrobial composition of claim 2 having a total concentration of 3-iodo-2-propynyl-butylcarbamate and fluometuron from 500 ppm to 3000 ppm.

* * * * *